US010080561B2

(12) United States Patent
Lauchner

(10) Patent No.: US 10,080,561 B2
(45) Date of Patent: *Sep. 25, 2018

(54) ADJUSTABLE CANNULA AND METHODS OF USE

(71) Applicant: Medtronic Holding Company Sárl, Tolochenaz (CH)

(72) Inventor: Craig Lauchner, Mountain View, CA (US)

(73) Assignee: Medtronic Holding Company Sárl, Tolochenaz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/848,757

(22) Filed: Dec. 20, 2017

(65) Prior Publication Data

US 2018/0132840 A1    May 17, 2018

Related U.S. Application Data

(62) Division of application No. 14/288,098, filed on May 27, 2014, now Pat. No. 9,848,864.

(51) Int. Cl.
*A61B 17/02* (2006.01)
*A61B 90/30* (2016.01)
*A61B 17/34* (2006.01)

(52) U.S. Cl.
CPC .......... *A61B 17/0293* (2013.01); *A61B 90/30* (2016.02); *A61B 17/3439* (2013.01); *A61B 2090/309* (2016.02)

(58) Field of Classification Search
CPC ............ A61B 17/3415; A61B 17/3417; A61B 17/3421; A61B 17/3423; A61B 17/3431; A61B 17/3439; A61B 2017/3422; A61B 8/4236; A61M 25/0023; A61M 29/00; A61M 2025/0024
See application file for complete search history.

(56) References Cited

U.S. PATENT DOCUMENTS

| | | | |
|---|---|---|---|
| 3,788,318 A | 1/1974 | Dusseau et al. | |
| 4,397,647 A | 8/1983 | Gordon | |
| 4,484,913 A | 11/1984 | Swauger | |
| 5,320,611 A | 6/1994 | Bonutti et al. | |
| 5,785,648 A | 7/1998 | Min | |

(Continued)

OTHER PUBLICATIONS

Medtronic, MeTRx® II System, 2008, Medtronic Sofamor Danek USA, Inc.

(Continued)

*Primary Examiner* — Anu Ramana

(57) ABSTRACT

A surgical instrument includes a first member including a groove. A second member includes an aperture and teeth configured to slidably engage the groove. A third member is positioned in the aperture and includes a passageway defining a first longitudinal axis and a flange. A fourth member is positioned in the passageway and includes a lip that engages the flange. The lip extends at an acute angle relative to a second longitudinal axis defined by the fourth member. A fifth member is rotatably disposed in the passageway and includes a first end surface that engages a second end surface of the fourth member defined by the lip. In a first configuration, the fourth member extends perpendicular to the first longitudinal axis. In a second configuration, the fourth member extends at an acute angle relative to the first longitudinal axis. Systems and methods are disclosed.

20 Claims, 6 Drawing Sheets

(56) References Cited

U.S. PATENT DOCUMENTS

| | | |
|---|---|---|
| 5,792,044 A | 8/1998 | Foley et al. |
| 5,902,231 A | 5/1999 | Foley et al. |
| 5,954,635 A | 9/1999 | Foley et al. |
| 6,007,487 A | 12/1999 | Foley et al. |
| 6,152,871 A | 11/2000 | Foley et al. |
| 6,162,170 A | 12/2000 | Foley et al. |
| 6,176,823 B1 | 1/2001 | Foley et al. |
| 6,206,822 B1 | 3/2001 | Foley et al. |
| 6,217,509 B1 | 4/2001 | Foley et al. |
| 6,425,859 B1 | 7/2002 | Foley et al. |
| 6,520,907 B1 | 2/2003 | Foley et al. |
| 6,679,833 B2 | 1/2004 | Foley et al. |
| 6,945,933 B2 | 9/2005 | Branch et al. |
| 7,196,596 B2 | 3/2007 | Foley et al. |
| 7,261,688 B2 | 8/2007 | Smith et al. |
| 7,374,534 B2 | 5/2008 | Dalton |
| 7,473,222 B2 | 1/2009 | Dewery et al. |
| 7,513,869 B2 | 4/2009 | Branch et al. |
| 7,524,285 B2 | 4/2009 | Branch et al. |
| 7,976,463 B2 | 7/2011 | Dewery et al. |
| 7,981,029 B2 | 7/2011 | Branch et al. |
| 7,981,030 B2 | 7/2011 | Smith et al. |
| 7,988,624 B2 | 8/2011 | Smith et al. |
| 7,993,378 B2 | 8/2011 | Foley et al. |
| 8,062,217 B2 | 11/2011 | Boucher et al. |
| 8,246,538 B2 | 8/2012 | Gorek |
| 8,517,935 B2 | 8/2013 | Marchek et al. |
| 8,622,897 B2 | 1/2014 | Raymond et al. |
| 2005/0192485 A1 | 9/2005 | Branch et al. |
| 2007/0100210 A1 | 5/2007 | Selover |
| 2012/0271357 A1 | 10/2012 | Arthur et al. |

OTHER PUBLICATIONS

Medtronic, MeTRx® System Cases, Product Catalog, 2008, Medtronic Sofamor Danek USA, Inc.

Medtronic, Mast Quadrant™ Retractor System Medial lateral Blades Procedural Solutions Technique, 2009 Medtronic Sofamor Danek USA, Inc.

Medtronic Sofamor Danek, METRx System Surgical Technique. Minimal Access Spinal Technologies, 2004 Medtronic Sofamor Danek USA. Inc.

Medtronic. Direct Lateral Interbody Fusion, DLIF Surgical Technique, 2011 Medtronic Sofamor Danek USA, Inc.

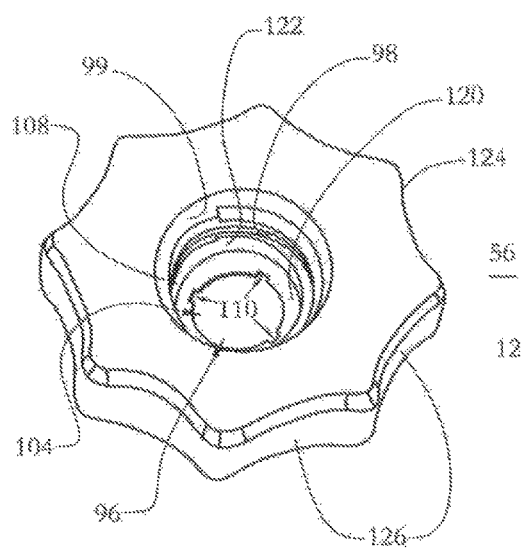
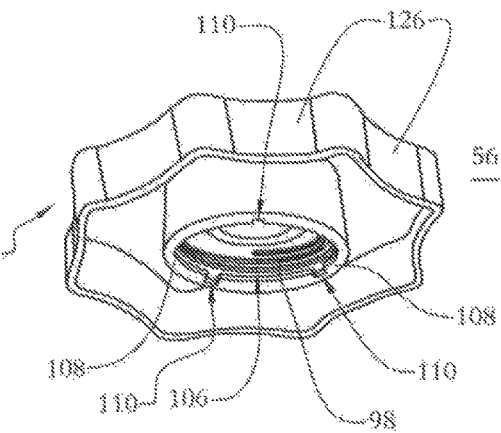
FIG. 6
FIG. 7
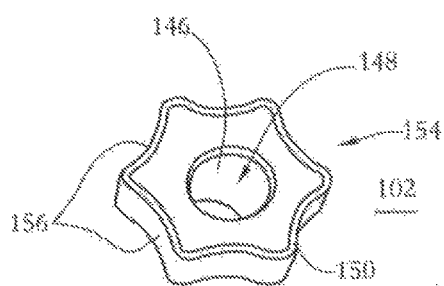
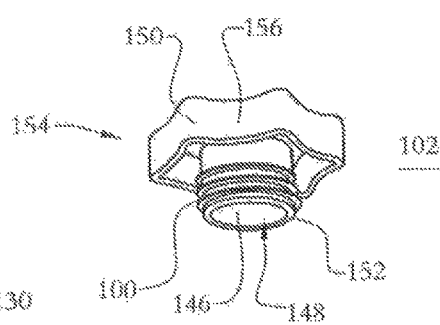
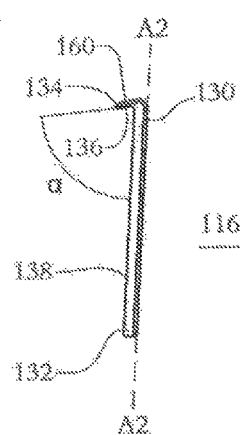
FIG. 8
FIG. 9
FIG. 10

ADJUSTABLE CANNULA AND METHODS OF USE

The present application is a divisional of U.S. application Ser. No. 14/288,098, filed May 27, 2014 (now U.S. Pat. No. 9,848,864); all of which is incorporated herein by reference.

TECHNICAL FIELD

The present disclosure generally relates to medical devices for the treatment of musculoskeletal disorders, and more particularly to a surgical system and method for accessing a surgical site to facilitate treatment.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. Surgical retractors may be employed during a surgical treatment to provide access and visualization of a surgical site. Such retractors space apart and support tissue and/or other anatomical structures to expose anatomical structures adjacent the surgical site and/or provide a surgical pathway to the surgical site. This disclosure describes an improvement over these prior art technologies.

SUMMARY

In one embodiment, a surgical instrument is provided. The surgical instrument comprises a first member comprising an inner surface defining an arcuate groove. A second member comprises a first portion including an inner surface defining an aperture and a second portion extending from the first portion and including a plurality of spaced apart teeth configured to slidably engage the groove. A third member is positioned in the aperture. The third member comprises an inner surface defining a passageway defining a first longitudinal axis. The inner surface of the third member includes a flange extending perpendicular to the first longitudinal axis. A fourth member is positioned in the passageway and comprises a lip that engages the flange. The lip extends at an acute angle relative to a second longitudinal axis defined by the fourth member. A fifth member is rotatably disposed in the passageway and comprises a first end surface that engages a second end surface of the fourth member defined by the lip. The fourth member is movable between a first configuration in which the first and second end surfaces are spaced apart and the fourth member extends perpendicular to the first longitudinal axis and a second configuration in which the first end surface engages the second end surface and the fourth member extends at an acute angle relative to the first longitudinal axis. In some embodiments, systems and methods are provided.

BRIEF DESCRIPTION OF THE DRAWINGS

The present disclosure will become more readily apparent from the specific description accompanied by the following drawings, in which:

FIG. 6 is a perspective view of a component shown in FIG. 1;

FIG. 7 is a perspective view of a component shown in FIG. 1;

FIG. 8 is a perspective view of a component shown in FIG. 1;

FIG. 9 is a perspective view of a component shown in FIG. 1; and

FIG. 10 is a perspective view of a component shown in FIG. 1.

DETAILED DESCRIPTION

Figure 1:
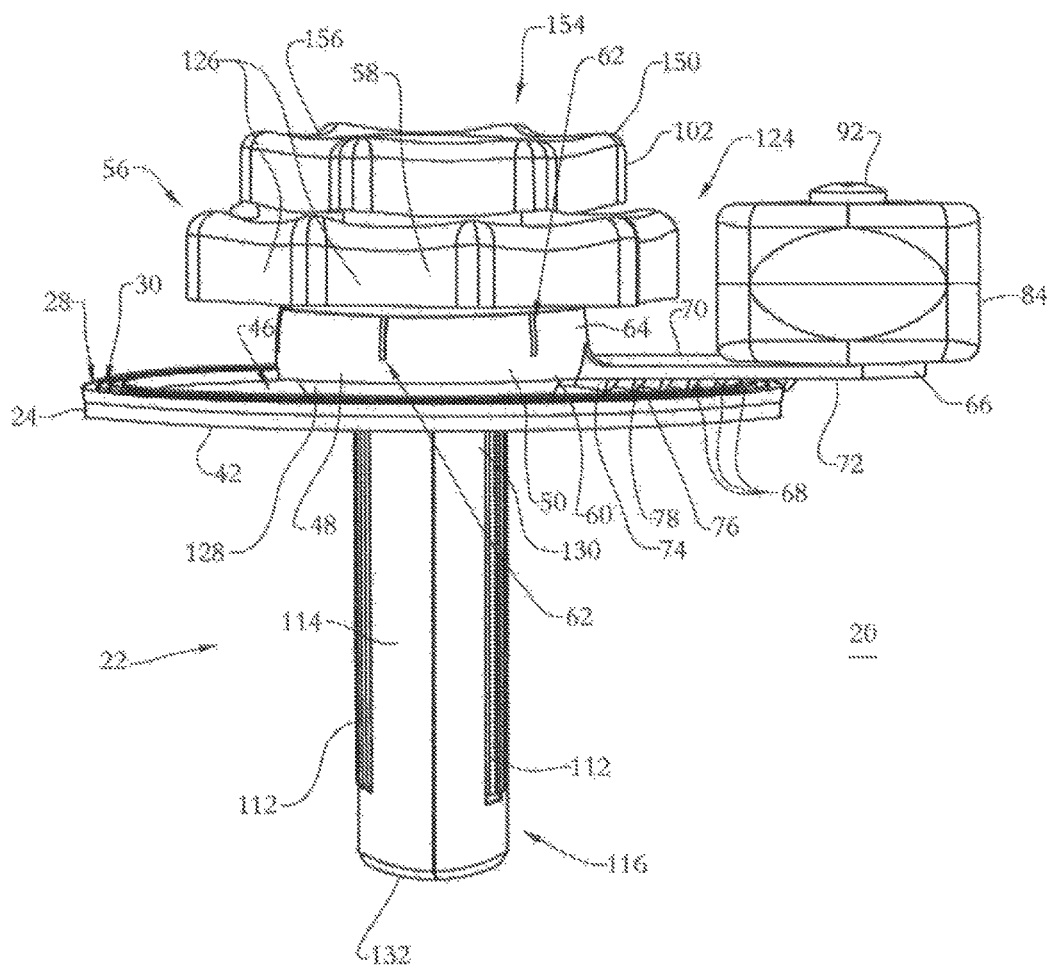
FIG. 1 is a perspective view of components of one embodiment of a surgical system in accordance with the principles of the present disclosure.

The exemplary embodiments of a surgical system and related methods of use disclosed are discussed in terms of medical devices for the treatment of musculoskeletal disorders and more particularly, in terms of a surgical system and method for accessing a surgical site to facilitate treatment. In one embodiment, the surgical system includes a surgical instrument or device that reduces costs and provides unique features that address unmet needs. In some embodiments, the device is made entirely from injection molded parts. In some embodiments, the device is disposable. In some embodiments, the device retracts in a circle or substantially in a circle to provide excellent visualization of a target site. In some embodiments, the device includes three integrated light emitting diodes (LEDs) near a distal tip for illuminating tissues without shadows, thereby increasing effective visualization.

In some embodiments, the device includes expanding leaves for tissue retraction. In some embodiments, the device is circumferentially continuous, eliminating the need for time consuming bleeding control. This feature allows a medical practitioner, such as, for example, a physician to save a good deal of time with cauterizing tools. This feature also allows the medical practitioner to accurately limit the expanded size of the cannula. In some embodiments, the device is circumferentially continuous by having a material, such as, for example, a fabric disposed about blades or members such that the material surrounds the blades as the blades expand and retract. In some embodiments, the device is configured for use by medical practitioners, such as, for example, interventionalists in connection with surgical procedures. In some embodiments, the device is configured for use in procedures in which the patient remains conscious. The device is configured to remain stationary as a patient moves, thus avoiding unintended movement of the surgical device, such as, for example, unintended dorsal movement. In some embodiments, the device includes a wag-and-hold notched ring that adheres to a patient, such as, for example, the skin of the patient. The wag-and-hold feature facilitates one-handed repositioning of the device in 360 degrees for improved visualization. This feature also allows for hands-free positioning of the device. Hands-free positioning is useful, for example, when a procedure, such as, for example, a lumbar decompression, starts on the ipsilateral side and then moves to the contralateral side. Stretching the incision and holding the device requires use of the hand-off in most cases.

In some embodiments, the present disclosure may be employed to treat spinal disorders such as, for example, degenerative disc disease, disc herniation, stenosis, tumor and fractures. In some embodiments, the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including posterior, posterior mid-line, lateral, and/or postero-lateral approaches, and in other body regions. The present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions of bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery, and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and methods of employing the surgical system in accordance with the principles of the present disclosure. Alternate embodiments are also disclosed. Reference will now be made in detail to the exemplary embodiments of the present disclosure, which are illustrated in the accompanying figures. Turning to FIGS. 1-10, there are illustrated components of a surgical system 20 including a surgical device, such as, for example, a retractor or cannula 22 in accordance with the principles of the present disclosure.

The components of surgical system 20 can be fabricated from biologically acceptable materials suitable for medical applications, including metals, synthetic polymers, ceramics and bone material and/or their composites, depending on the particular application and/or preference of a medical practitioner. For example, the components of surgical system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL®. manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancelous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytymosine carbonate, polycaroplaetohe and their combinations. Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

Cannula 22 includes a first member, such as, for example, a circular ring 24 comprising inner surfaces 26 defining grooves 28, 30. Groove 28 is spaced apart from groove 30. Groove 28 has a radius of curvature that is greater than that of groove 30. Groove 28 is defined by a pair of spaced apart projections 32, 34 and a planar bottom surface 36. Groove 30 is defined by projection 34, a projection 38 that is spaced apart from projection 34 and a planar bottom surface 40. Surfaces 36, 40 each extend parallel to a planar lower surface 42 of ring 22. Projections 32, 34, 38 each extend at an acute angle relative to surface 42 and/or surfaces 36, 40. Projection 32 includes an inner wall 32a and an outer wall 32b; projection 34 includes an inner wall 34a and an outer wall 34b; and projection 38 includes an inner wall 38a and an outer wall 38b. Walls 32a, 34a, 38a extend at the same angle relative to surface 42 and/or surfaces 36, 40. In some embodiments, walls 32a, 34a, 38a extend at an acute angle relative to surface 42 and/or surfaces 36, 40. Walls 32b, 34b, 38b extend at the same angle relative to surface 42 and/or surfaces 36, 40. In some embodiments, walls 32b, 34b, 38b extend at an acute angle relative to surface 42 and/or surfaces 36, 40. In some embodiments, walls 32a, 34a, 38a extend at an angle relative to surface 42 and/or surfaces 36, 40 that is different than that of walls 32b, 34b, and 38b. In some embodiments, walls 32a, 34a, 38a extend at an angle relative to surface 42 and/or surfaces 36, 40 that is greater than that of walls 32b, 34b, and 38b. Ring 24 defines a pathway 46 having a circular cross sectional configuration.

In some embodiments, ring 24 is variously shaped, such as, for example, circular, oval, oblong, triangular, square, polygonal, irregular, uniform, non-uniform, undulating, arcuate and/or variable. In some embodiments, projections 32, 34, 38 each extend at an angle between about 15 degrees and about 75 degrees relative to surface 42 and/or surfaces 36, 40. In some embodiments, walls 32a, 34a, 38a and/or walls 32b, 34b, 38b each extend at an angle between about 30 degrees and about 60 degrees relative to surface 42 and/or surfaces 36, 40. In some embodiments, walls 32a, 34a, 38a and/or walls 32b, 34b, 38b each extend at an angle of about 45 degrees relative to surface 42 and/or surfaces 36, 40. In some embodiments, walls 32a, 34a, 38a and/or walls 32b, 34b, 38b may be disposed at alternate orientations, relative to surface 42 and/or surfaces 36, 40, such as, for example, transverse, perpendicular and/or other angular orientations such as acute or obtuse and/or may be offset or staggered. In some embodiments, surface 42 may have various surface configurations, such as, for example, smooth and/or surface configurations to enhance fixation with tissue, such as, for example, the skin of a patient, such as, for example, rough, arcuate, undulating, porous, semi-porous, dimpled, polished and/or textured. In some embodiments, a removable liner is attached to surface 42. An adhesive is applied to the removable liner to adhere the removable liner to the patient. In some embodiments, pathway 46 may have various cross section configurations, such as, for example, circular, oval, oblong, triangular, rectangular, square, polygonal, irregular, uniform, non-uniform, variable, tubular and/or tapered. In some embodiments, ring 24 is made from plastic, such as, for example, molded plastic.

A second member, such as, for example, a positioning member 48 comprises a portion 50 including an inner surface 52 defining an aperture 54 having a substantially spherical cross sectional configuration configured for disposal of a third member, such as, for example, a holding member 56, as will be discussed. In some embodiments, aperture 54 is concavely curved between a top end 58 of portion 50 and an opposite bottom end 60 of portion 50 such that a middle portion of aperture 54 has a maximum diameter or width that is greater than that of aperture 54 adjacent end 58 or end 60. In some embodiments, aperture 54 is continuously curved between ends 58, 60. In some embodiments, member 48 includes spaced apart slits 62 extending through surface 52 and an opposite outer surface 64 configured to allow aperture 54 to expand and contract as member 56 is inserted into and removed from aperture 54. In some embodiments, member 48 comprises one or a plurality of slits 62. In some embodiments, slits 62 are disposed radially about member 48. In some embodiments, slits 62 are evenly spaced apart from one another. In some embodiments, slits 62 extend parallel to a longitudinal axis defined by member 48. In some embodiments, slits 62 extend through an upper end surface of member 48 without extending through a lower end surface of member 48, as shown in FIG. 1, for example. In some embodiments, slits 62 extend through the lower end surface of member 48 without extending through the upper end surface of member 48. In some embodiments, member 48 includes slits 62 extending through the upper end surface of member 48 and the lower end surface of member 48. In some embodiments, slits 62 extending through the upper end surface of member 48 are aligned with slits 62 extending through the lower end surface of member 48. In some embodiments, slits 62 extending through the upper end surface of member 48 alternate with slits 62 extending through the lower end surface of member 48. In some embodiments, member 48 and/or member 56 are made from plastic, such as, for example, molded plastic.

Member 48 includes a portion 66 extending from portion 50. Portion 66 includes a plurality of spaced apart teeth 68 configured to slidably engage at least one of grooves 28, 30 to couple member 48 with ring 24. Portion 66 includes a planar upper surface 70 and an opposite planar lower surface 72. Surface 70 extends parallel to surface 72. Teeth 68 each extend at an acute angle relative to surface 70 and/or surface 72. Teeth 68 each include side surfaces 74, 76 extending from surface 72. A planar end surface 78 extends between surfaces 74, 76. Surfaces 78 each extend parallel to surface 70 and/or surface 72. Surfaces 74 extend at the same angle relative to surface 70 and/or surface 72. In some embodiments, surfaces 74 each extend at an acute angle relative to surface 70 and/or surface 72. Surfaces 76 extend at the same angle relative to surface 70 and/or surface 72. In some embodiments, surfaces 76 each extend at an acute angle relative to surface 70 and/or surface 72. In some embodiments, surfaces 74 extend at an angle relative to surface 70 and/or surface 72 that is different than that of surfaces 76. In some embodiments, surfaces 74 extend at an angle relative to surface 70 and/or surface 72 that is greater than that of surfaces 76.

In some embodiments, teeth 68 each extend at an angle between about 15 degrees and about 75 degrees relative to surface 70 and/or surface 72. In some embodiments, surfaces 74 and/or surfaces 76 each extend at an angle between about 30 degrees and about 60 degrees relative to surface 70 and/or surface 72. In some embodiments, surfaces 74 and/or surfaces 76 each extend at an angle of about 45 degrees relative to surface lip 134 and/or surface 72. In some embodiments, surfaces 74 and/or surfaces 76 may be disposed at alternate orientations, relative to surface 70 and/or surface 72, such as, for example, transverse, perpendicular and/or other angular orientations such as acute or obtuse and/or may be offset or staggered.

Figure 3:
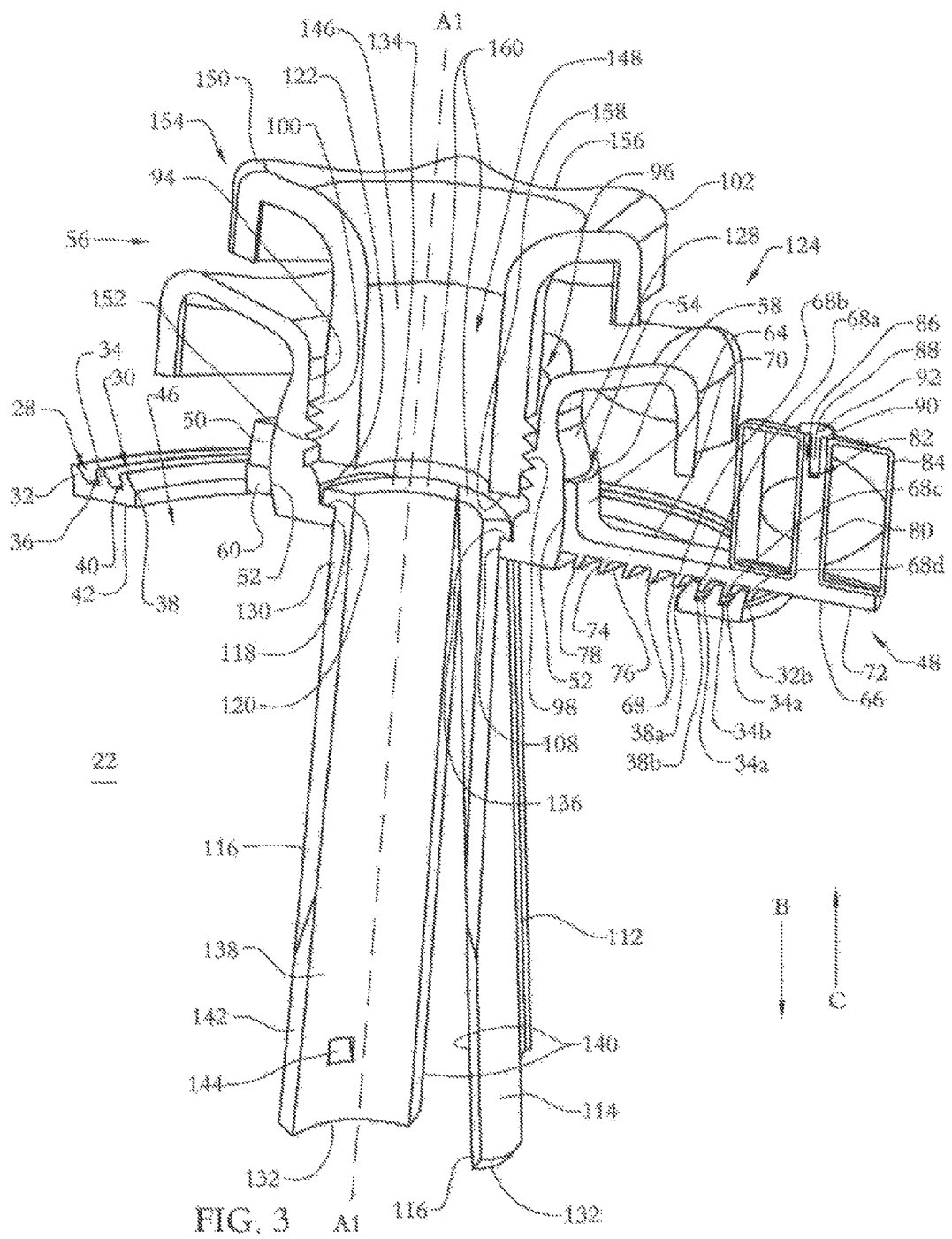
FIG. 3 is a perspective, cross sectional view of components shown in FIG. 1.

As shown in FIG. 3, for example, when a respective tooth 68*a* is disposed in groove 30, surface 74 of tooth 68*a* engages wall 38*b* and surface 76 of tooth 68*a* engages wall 34*a*. When surface 74 of tooth 68*a* engages wall 38*b* and surface 76 of the tooth 68 engages wall 34*a*, surface 78 of tooth 68*a* engages surface 36. When tooth 68*a* is disposed in groove 30, surface 76 of a first adjacent tooth 68*b* engages wall 38*a*. In some embodiments, when surface 76 of tooth 68*b* engages wall 38*a*, surface 74 of a second adjacent tooth 68*c* engages wall 34*b* and surface 76 of tooth 68*c* engages wall 32*a*. When surface 74 of tooth 68*c* engages wall 34*b* and surface 76 of tooth 68*c* engages wall 32*a*, surface 78 of tooth 68*c* engages surface 40. In some embodiments, when tooth 68*c* is disposed in groove 30, surface 74 of a third adjacent tooth 68*d* engages wall 32*b*. This configuration allows teeth 68*a*, 68*c* to slide within grooves 28, 30 as member 48 moves relative to ring 24 without teeth 68 falling out of grooves 28, 30.

In some embodiments, portion 66 includes an extension 80 extending perpendicular to surface 72 and/or surface 74. Extension 80 extends from surface 70 and includes a blind hole 82. A handle 84 includes an inner surface defining a channel 86 having extension 80 disposed therein such that handle 84 is rotatable about extension 80. A shaft 88 of a pin 90 is disposed in hole 82 such that a head 92 of pin 90 covers channel 86. Head 92 has a maximum width or diameter that is greater than that of channel 86 to prevent head 92 from falling through channel 86. Handle 84 is configured for gripping by a medical practitioner to move member 48 relative to ring 24, such as, for example, to rotate member 48 about an axis defined by pathway 46. In some embodiments, pin 90 can be variously connected with extension 80, such as, for example, monolithic, integral connection, frictional engagement, threaded engagement, mutual grooves, screws, adhesive, nails, barbs and/or raised element.

Member 56 comprises an inner surface 94 defining a passageway 96. Passageway 96 includes a proximal portion and a distal portion. The proximal portion of passageway 96 has a maximum diameter that is greater than that of the distal portion of passageway 96. The proximal portion of passageway 96 includes an interior thread form 98 configured to engage an exterior thread form 100 of a fifth member, such as, for example, a locking member 102, to couple member 56 with member 102, as will be discussed. In some embodiments, member 102 can be variously connected with member 56, such as, for example, monolithic, integral connection, frictional engagement, threaded engagement, mutual grooves, screws, adhesive, nails, barbs and/or raised element. In some embodiments, member 56 and/or member 102 are made from plastic, such as, for example, molded plastic.

Passageway 96 extends through a circular opening 104 in a proximal end of member 56 and a substantially circular opening 106 in a distal end of member 56. Passageway 96 defines a first longitudinal axis A1 extending between the proximal and distal ends of member 56. Opening 106 is defined, at least in part, by an annular flange 108 extending perpendicular to axis A1. In some embodiments, flange 108 includes one or a plurality of slots 110 configured for disposal of a ridge 112 projecting from an outer surface 114 of a fourth member, such as, for example, a blade 116. Slots 110 are disposed radially about flange 108 and are evenly spaced apart from one another. Slots 110 each have a depth that is substantially equivalent to a height of each of ridges 112 such that surface 114 engages an inwardly facing end surface 118 of flange 108. Flange 108 is continuously curved between adjacent slots 110.

In some embodiments, opening 104 and/or opening 106 can have various shape configurations, such as, for example, oval, oblong, square, triangular, rectangular, hexagonal, polygonal, irregular, uniform, non-uniform, variable and/or tapered. In some embodiments, the number of slots 110 in flange 108 is equal to the number of blades 116 of cannula 22. In some embodiments, cannula 22 includes one or a plurality of blades 116. In one embodiment, cannula 22 includes three blades 116. In some embodiments, cannula 22 includes six blades 116. In some embodiments, surface 114 is convexly curved between opposite axial surfaces, such as, for example, planar side surfaces 140, 142. In some embodiments, surface 114 is continuously curved between surfaces 140, 142. In some embodiments, at least one of blades 116 is made from plastic, such as, for example, molded plastic. In some embodiments, at least one of blades 116 is made from stainless steel to provide strength.

Flange 108 includes a top surface 120 that extends perpendicular to axis A1. Surface 120 abuts an inner wall 122 of member 56 that extends perpendicular to surface 120 such that wall 122 is parallel with axis A1. In some embodiments, flange 108 and/or surface 120 may be disposed at alternate orientations, relative to axis A1, such as, for example, transverse, perpendicular and/or other angular orientations such as acute or obtuse, co-axial and/or may be offset or staggered. In some embodiments, wall 122 may be disposed at alternate orientations, relative to axis A1 and/or surface 120, such as, for example, transverse, perpendicular and/or other angular orientations such as acute or obtuse, co-axial and/or may be offset or staggered. In some embodiments, the proximal end of member 56 includes a gripping portion 124 comprising a plurality of notches 126 configured for gripping by a medical practitioner to selectively rotate member 56 about axis A1.

Member 56 is positioned in aperture 54 such that an outer surface 128 of member 56 engages surface 52. In some embodiments, member 56 is rotatably disposed in aperture 54 such that member 56 can pivot within aperture 54 through one or a plurality of planes and/or axes. In some embodiments, surface 128 is convexly curved between a distal end surface of member 56 and portion 124. In some embodiments, surface is continuously curved between the distal end surface of member 56 and portion 124. In some embodiments, the convex configuration of surface 128 and the concave configuration of aperture 54 allow member 56 to rotate within aperture 54 through one or a plurality of planes and/or axes.

Proximal portions of blades 116 are positioned in passageway 96. Blades 116 each extend along a second longitudinal axis A2 between an end 130 and an opposite end 132. Ends 130 each comprise a lip 134 extending at an angle α relative to a respective axis A2. A bottom surface 136 of each lip 134 engages surface 120 of flange 108 to couple blades 116 with member 56. In particular, ridge 112 of a respective one of blades 116 is positioned in one of slots 110 to prevent the blade 116 from rotating relative to member 56. When ridge 112 is positioned in the slot 110, the blade 116 is movable along axis A1 in the direction shown by arrow B and the direction shown by arrow C. Surface 114 slides along surface 118 as the blade moves along axis A1 in the direction shown by arrow B or the direction shown by arrow C. The blade 116 is movable along axis A1 in the direction shown by arrow B until surface 136 engages surface 120. In some embodiments, angle α is an acute angle. In some embodiments, angle α is angle between 45 and 90 degrees. In some embodiments, lip 134 may be disposed at alternate orientations, relative to axis A2, such as, for example, transverse, perpendicular and/or other angular orientations such as acute or obtuse, co-axial and/or may be offset or staggered.

Blades 116 each comprise an inner surface 138 that is concavely curved between axial side surfaces 140, 142. In some embodiments, surface 138 is continuously curved between surfaces 140, 142. In some embodiments, surface 138 is planar or flat and comprises sheet metal. In some embodiments, cannula 22 includes fabric between blades 116 so as to form a sheath or sleeve around blades 116 that allows blades 116 to move between first and second configurations discussed hereinbelow. In some embodiments, surface 138 includes a light source 144, such as, for example a light emitting diode (LED) at end 132. Light source 144 is configured to project light away from surface 138. In some embodiments, light source 144 is embedded between surface 138 and surface 114 such that light source 144 is embedded in a wall thickness of blade 116. In some embodiments, light source 144 is applied to surface 138 such that light source 144 does not extend into surface 138. In some embodiments, light source 144 is bonded or otherwise adhered to surface 138 using a glue or adhesive. In some embodiments, light source 144 extends into surface 138 without extending through surface 114. In some embodiments, all or only a portion of surface 140 and/or surface 142 may be variously configured and dimensioned, such as, for example, planar, concave, polygonal, irregular, uniform, non-uniform, staggered, tapered, consistent or variable. In some embodiments, each blade 116 includes a light source 144.

In some embodiments, blade 116 includes a power source, such as, for example, a battery to provide power to light source 144. In some embodiments, light source 144 is powered by an external power source. In some embodiments, blade 116 and/or light source 144 includes a switch, such as, for example, an on/off switch to move light source 144 between an on position in which light source 144 emits light and an off position in which light source 144 does not emit light.

Member 102 is rotatably disposed in passageway 96 such that thread form 98 engages thread form 100. Rotating member 102 relative to member 56 about axis A1 in a first direction, such as, for example, clockwise or counterclockwise moves member 102 relative to member 56 in the direction shown by arrow B. Rotating member 102 relative to member 56 about axis A1 in a second direction, such as, for example, clockwise or counterclockwise moves member 102 relative to member 56 in the direction shown by arrow C. An inner surface 146 of member 102 defines a lumen 148 that is in communication with passageway 96. Member 102 includes a first end 150 and an opposite second end 152. End 150 includes a gripping portion 154 comprising a plurality of notches 156 configured for gripping by a medical practitioner to selectively rotate member 102 about axis A1. End 152 includes a planar end surface 158 configured to engage top surfaces 160 of lips 134. Surface 158 extends perpendicular to axis A1. In some embodiments, surface 158 may be disposed at alternate orientations, relative to axis A1, such as, for example, transverse, perpendicular and/or other angular orientations such as acute or obtuse, co-axial and/or may be offset or staggered.

In assembly, operation and use, surgical system 20, similar to that described above, is employed, for example, with a minimally invasive surgical procedure for spinal and neurosurgical applications with a patient. For example, during spine surgery, a surgeon will make an incision in the skin of a patient's back over vertebrae to be treated. One or more dilators may be employed to gradually separate the muscles and create a portal through which the surgery may be performed.

Ring 24 is coupled to a patient such that the incision is visible through pathway 46. In some embodiments, ring 24 is positioned relative to the patient such that the incision is centrally located within pathway 46. In some embodiments, a glue or other adhesive material is applied to surface 42 such that the adhesive binds to the skin of the patient to fix ring 24 relative to the patient. In some embodiments, surface 42 includes surface configurations to enhance fixation with skin to prevent movement of ring 24 relative to the patient and/or limit movement of ring 24 relative to the patient, such as, for example, rough, arcuate, undulating, porous, semiporous, dimpled, polished and/or textured.

Figure 2:
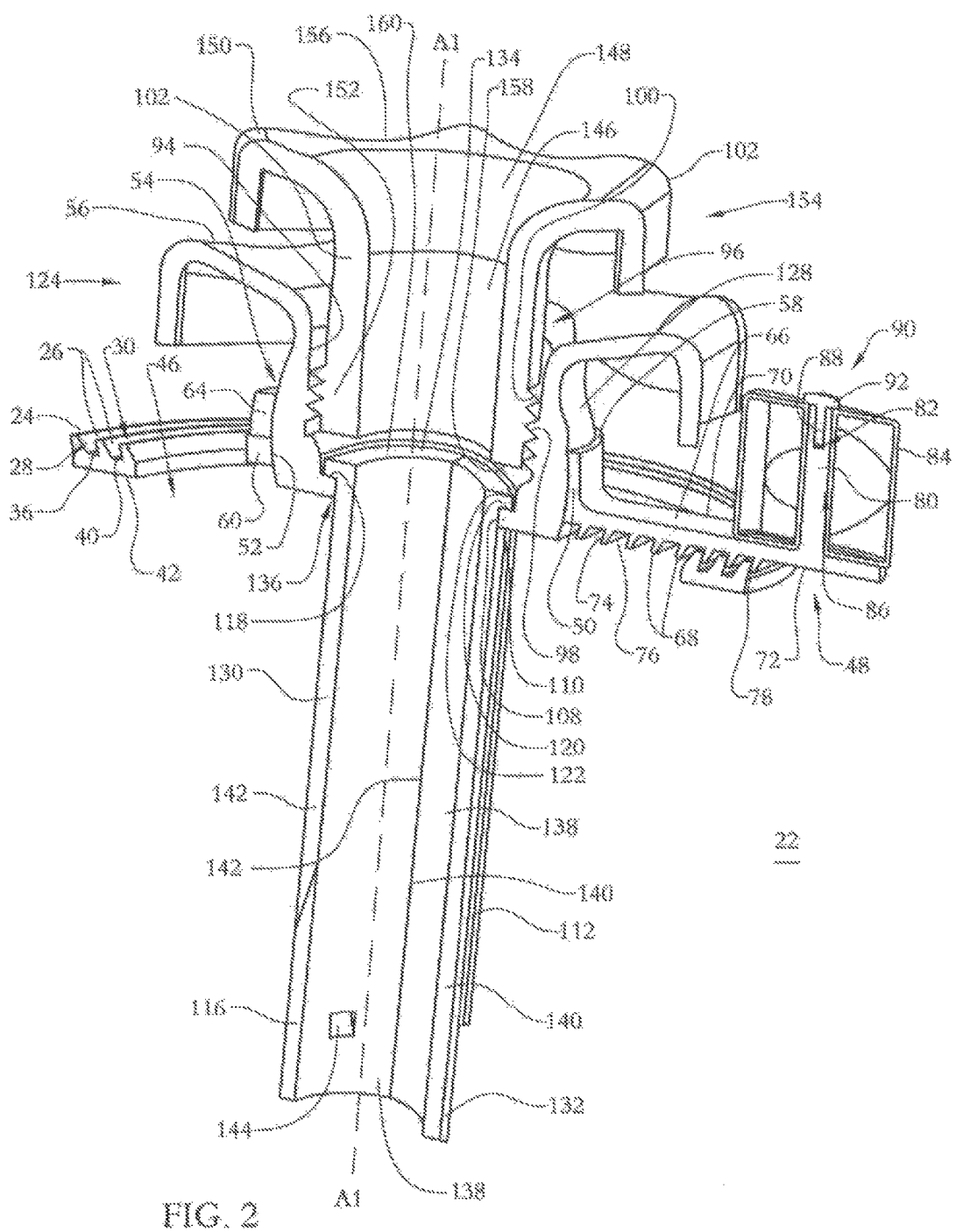
FIG. 2 is a perspective, cross sectional view of components shown in FIG. 1.
Figure 4:
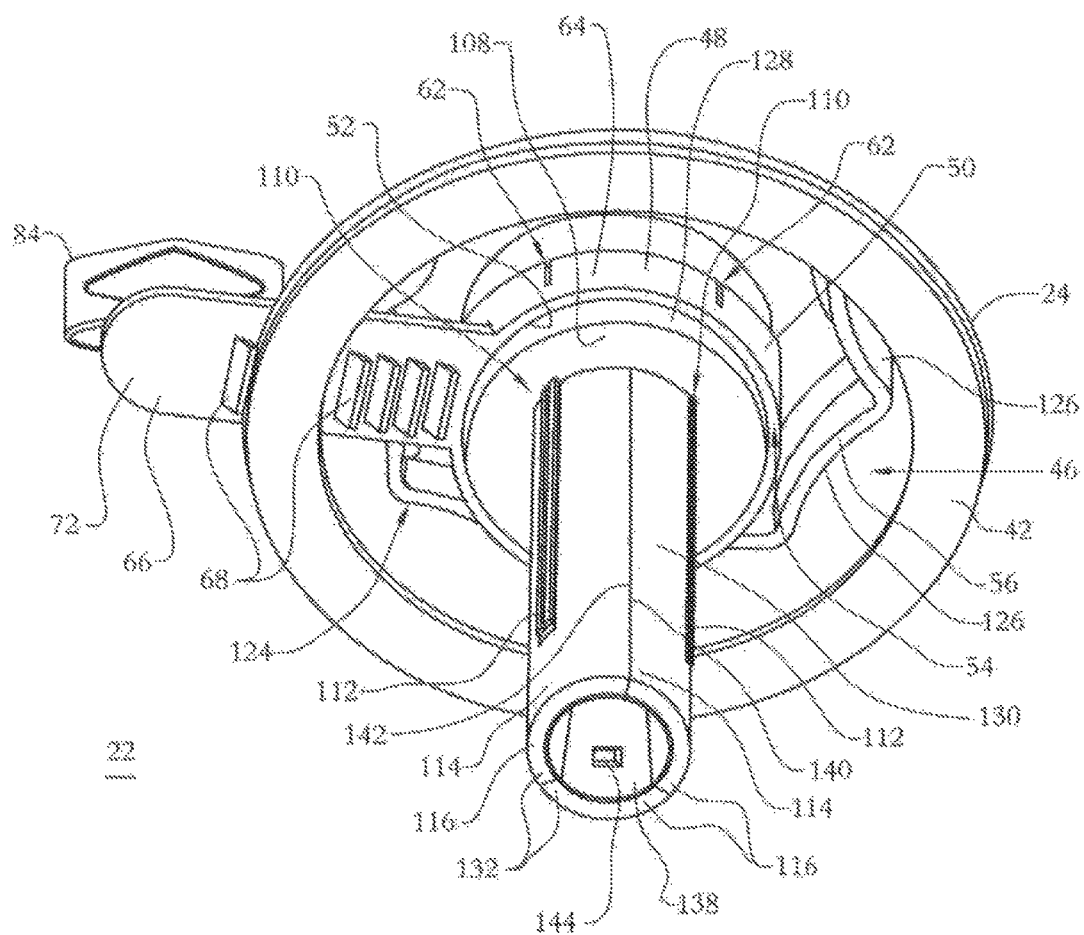
FIG. 4 is a perspective, bottom view of components shown in FIG. 1.

Member 102 is positioned in passageway 96 with blades 116 in a first configuration such that surface 158 is spaced apart from lips 134 and blades 116 each extend parallel to axis A1, as shown in FIG. 2 and FIG. 4. When blades 116 are in the first configuration, surface 140 of a respective blade 116 engages surface 142 of an adjacent blade 116 and surface 142 of the respective blade 116 engages surface 140 of an opposite adjacent blade 116 such that blades 116 form a tubular structure, as shown in FIG. 2 and FIG. 4. That is, when blades 116 are in the first configuration, surfaces 138 define a conduit having a cylindrical cross sectional configuration, as shown in FIG. 4.

Member 56 is coupled with member 48 by positioning member 56 in aperture 54 such that surface 128 engages surface 52. In some embodiments, member 56 is rotatable relative to member 48 when member 56 is positioned in aperture 54. In some embodiments, member 56 is rotated relative to member 48 to a selected orientation or trajectory when member 56 is positioned in aperture 54. For example, member 56 may be rotated relative to member 48 such that an axis defined by aperture 54 extends transverse to axis A1 and/or is offset from axis A1. In some embodiments, member 48 comprises a resilient material such that slits 62 expand from a non-expanded configuration to an expanded configuration as member 56 is inserted into aperture 54 and slits 62 return to the non-expanded configuration after member 56 is inserted into aperture 54.

Blades 116 are inserted through pathway 46 and into the incision. As blades 116 are inserted into the incision, member 48 is positioned relative to ring 24 such that two of teeth 68 are aligned with grooves 28, 30. In one embodiment, shown in FIG. 3, the two teeth 68 are positioned within grooves 28, 30 such that when a respective tooth 68*a* is disposed in groove 30, surface 74 of tooth 68*a* engages wall 38*b* and surface 76 of tooth 68*a* engages wall 34*a*. When surface 74 of tooth 68*a* engages wall 38*b* and surface 76 of the tooth 68 engages wall 34*a*, surface 78 of tooth 68*a* engages surface 36. When tooth 68*a* is disposed in groove 30, surface 76 of a first adjacent tooth 68*b* engages wall 38*a*. In some embodiments, when surface 76 of tooth 68*b* engages wall 38*a*, surface 74 of a second adjacent tooth 68*c* engages wall 34*b* and surface 76 of tooth 68*c* engages wall 32*a*. When surface 74 of tooth 68*c* engages wall 34*b* and surface 76 of tooth 68*c* engages wall 32*a*, surface 78 of tooth 68*c* engages surface 40. In some embodiments, when tooth 68*c* is disposed in groove 30, surface 74 of a third adjacent tooth 68*d* engages wall 32*b*. This configuration allows teeth 68*a*, 68*c* to slide within grooves 28, 30 as member 48 moves relative to ring 24 without teeth 68 falling out of grooves 28, 30. In some embodiments, teeth 68 are inserted into grooves 28, 30 to couple member 48 with ring 24 prior to adhering ring 24 to the skin of the patient.

In some embodiments, teeth 68b, 68c may be removed from grooves 28, 30 and other teeth 68 are positioned relative to grooves 28, 30 in the same manner as teeth 68a-d discussed above. This allows the medical practitioner to adjust the distance of aperture 54 relative to ring 24. For example, if the medical practitioner wishes to position aperture 54 closer to ring 24, teeth 68 closer to aperture 54 are inserted into grooves 28, 30. If, on the other hand, the medical practitioner wishes to position aperture 54 further from ring 24, teeth farther from aperture 54 are inserted into grooves 28, 30. In that member 48 comprises a plurality of uniformly spaced apart teeth 68, this configuration allows the medical practitioner to incrementally adjust the distance between aperture 54 and ring 24.

Once the appropriate teeth 68 are positioned in grooves 28, 30, the medical practitioner may adjust the position of member 48 relative to ring 24 and/or pathway 46 by moving member 48 relative to ring 24 such that teeth 68 translate within grooves 28, 30 without teeth 68 falling out of grooves 28, 30. That is, grooves 28, 30 act as tracks that teeth 68 slide within to move member 48 about an axis defined by pathway 46. In some embodiments, the medical practitioner manipulates handle 84 to rotate member 48 about ring 24. Member 48 may be rotated about ring 24 until member 48 is selectively positioned relative to ring 24 and/or pathway 46.

Figure 5:
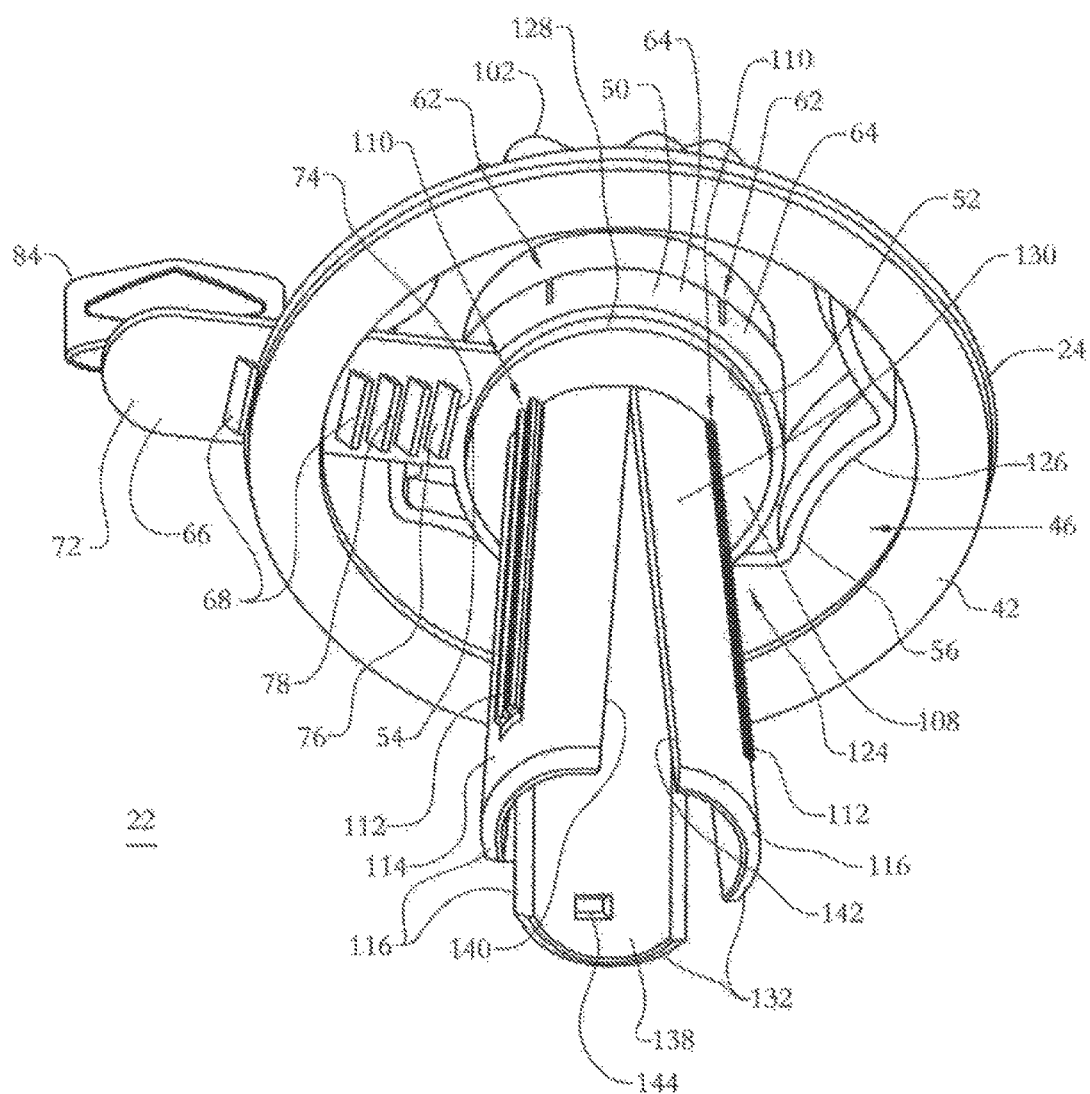
FIG. 5 is a perspective, bottom view of components shown in FIG. 1.

Once member 48 is selectively positioned relative to ring 24 and/or pathway 46, blades 116 are moved from the first configuration to a second configuration such that surface 158 engages lips 134 and blades 116 each extend transverse to axis A1, as shown in FIG. 3 and FIG. 5, to create a passageway or portal to the surgical site. To move blades 116 from the first configuration to the second configuration, member 102 is rotated relative to member 56 about axis A1 in a first direction, such as, for example, clockwise or counterclockwise, causing member 102 to move relative to member 56 in the direction of arrow B. Member 102 is rotated relative to member 56 in the first direction until surface 158 engages surfaces 160 to exert a force on blades 116. Due to the transverse orientation of lips 134, the force causes blades 116 to deflect outwardly away from axis A1 such that blades 116 extend at an acute angle relative to axis A1, as shown in FIGS. 3 and 5. When blades 116 extend at an acute angle relative to axis A1, blades 116 are in the second configuration. When blades 116 are in the second configuration, surface 140 of a respective blade 116 is spaced apart from surface 142 of an adjacent blade 116 at least at ends 132 and surface 142 of the respective blade 116 is spaced apart from surface 140 of an opposite adjacent blade 116 at least at ends 132, as shown in FIGS. 3 and 5.

When blades 116 are in the second configuration, surfaces 114 engage tissue, such as, for example, soft tissue, ligaments, tendons, cartilage and/or bone. Blades 116 space apart tissue and create access and/or a surgical pathway to a surgical site. That is, when blades 116 are in the second configuration, an item, such as, for example, a surgical instrument may be inserted through lumen 148 and passageway 96 and into a conduit defined by surfaces 138. In some embodiments, light sources 144 are in an on position as blades 116 move from the first configuration to the second configuration. In some embodiments, light sources 144 are moved from an off position to an on position after blades 116 are moved from the first configuration to the second configuration. When light sources 144 are in an on position, light sources 144 emit light into the conduit defined by surfaces 138 to aid in visualization to perform a surgical procedure, for example. In some embodiments, light sources 144 are configured to emit light without creating shadows, making cannula 22 useful for imaging purposes, for example. In some embodiments, at least one of blades 116 includes at least one light source 144 at end 130. In some embodiments, at least one of blades 116 includes at least one light source 144 at end 130 and at least one light source 144 at end 132. In some embodiments, at least one of blades 116 also includes at least one light source 144 between ends 130, 132. In some embodiments, blades 116 are inserted into the incision when blades 116 are in the second configuration.

Upon completion of the surgical procedure, member 102 is rotated relative to member 56 in a second direction, such as, for example, clockwise or counterclockwise such that member 102 moves relative to member 56 in the direction shown by arrow C. Member 102 is rotated relative to member 56 in the second direction until surface 158 is spaced apart from surfaces 160 to move blades 116 from the second configuration, shown in FIGS. 3 and 5, to the first configuration, shown in FIGS. 2 and 4. Blades 116 and members 48, 56, 102 may be removed as an assembly by disengaging teeth 68 from grooves 28, 30 and translating blades 116 and members 48, 56, 102 in the direction shown by arrow C. After blades 116 and members 48, 56, 102 are removed, ring 24 may be removed from the patient's body. In some embodiments, after blades 116 and members 48, 56, 102 are removed; ring 24 remains in place and two of teeth 68 are inserted into grooves 28, 30 in the manner discussed above. Blades 116 are inserted into the incision in the first configuration, and are subsequently moved from the first configuration to the second configuration in the manner described above.

It is envisioned that the use of microsurgical and image guided technologies may be employed to access, view and repair spinal deterioration or damage, with the aid of cannula 22. It is contemplated that a surgical procedure may employ other instruments that can be mounted with cannula 22, such as, for example, nerve root retractors, tissue retractors, forceps, cutter, drills, scrapers, reamers, rongeurs, taps, cauterization instruments, irrigation and/or aspiration instruments, illumination instruments, inserter instruments and/or separators, such as, for example, one or more burrs.

Cannula 22 may be employed for performing spinal surgeries, such as, for example, laminectomy, discectomy, fusion, laminotomy, nerve root retraction, foramenotomy, facetectomy, decompression, spinal nucleus or disc replacement and procedures using bone graft and implantable prosthetics including plates, rods, and bone engaging fasteners.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

I claim:

1. A surgical method comprising:
    creating an incision in the skin of a patient;
    creating a surgical pathway from the incision to a surgical site within the patient;
    attaching a first surface of a first member to the skin of the patient, the first member including the first surface, an opposite second surface, an aperture extending between the first surface and the second surface, and an arcuate groove in the second surface;
    positioning two blade portions of a second member in the pathway, each of the two blade portions terminating in a lip portion, the two blade portions and the lip portions being received through a passageway of a third member, and the lip portions being positioned in the passageway between a flange portion of the third member and a fourth member rotatably disposed in the passageway;

moving the two blade portions of the second member from a closed first configuration to an open second configuration to create a working channel by contacting a first end surface provided on the fourth member with second end surfaces provided on the lip portions; and contacting one of a plurality of spaced apart teeth of a fifth member attached to the third member to the arcuate groove.

2. The surgical method of claim 1, wherein the third member is positioned at least adjacent the aperture in the first member.

3. The surgical method of claim 1, wherein the arcuate groove comprises spaced apart first and second circular grooves each having a different radius of curvature; and further comprising removing the one of the plurality of spaced apart teeth from the first groove and inserting the one of the plurality of spaced apart teeth into the second groove to move the fifth member relative to the first member.

4. The surgical method of claim 1, further comprising slidably moving the one of the plurality of spaced apart teeth in the arcuate groove from a first position to a second positon to move the fifth member relative to the first member.

5. The surgical method of claim 1, wherein the fourth member is rotatable relative to the third member such that the fifth member translates along a first longitudinal axis of the passageway.

6. The surgical method of claim 5, wherein rotatable movement of the fourth member within the passageway causing translation toward the second member causes contact of the first end surface with the second end surfaces.

7. The surgical method of claim 6, wherein contact of the first end surface with the second end surfaces first moves the two blade portions from the closed first configuration to the open second configuration, and second moves the two blade portions from the open second configuration to an open third configuration, the two blade portions being farther apart from one another in the open second configuration than the open third configuration.

8. A surgical method comprising:

creating an incision in the skin of a patient;

creating a surgical pathway from the incision to a surgical site within the patient;

attaching a first surface of a first member to the skin of the patient, the first member including the first surface, an opposite second surface, an aperture extending between the first surface and the second surface, and an arcuate groove provided on the second surface;

positioning a blade portion of a second expandable member in the pathway, and positioning a rim portion of the second expandable member in a passageway of a third member between a flange portion of the third member and a fourth member rotatably disposed in the passageway;

expanding the second member by contacting a first end surface provided on the fourth member with a second end surface provided on the rim portion of the second expandable member; and contacting one of a plurality of spaced apart teeth of a fifth member attached to the third member to the arcuate groove.

9. The surgical method of claim 8, wherein the third member is positioned at least adjacent the aperture in the first member.

10. The surgical method of claim 8, wherein the arcuate groove comprises spaced apart first and second circular grooves each having a different radius of curvature; and further comprising removing the one of the plurality of spaced apart teeth from the first groove and inserting the one of the plurality of spaced apart teeth into the second groove to move the fifth member relative to the first member.

11. The surgical method of claim 8, further comprising slidably moving the one of the plurality of spaced apart teeth in the arcuate groove from a first position to a second positon to move the fifth member relative to the first member.

12. The surgical method of claim 8, wherein the fourth member is rotatable relative to the third member such that the fifth member translates along a first longitudinal axis of the passageway.

13. The surgical method of claim 12, wherein rotatable movement of the fourth member within the passageway causing translation toward the second member causes contact of the first end surface with the second end surface.

14. The surgical method of claim 13, wherein contact of the first end surface with the second end surface first moves the blade portion from a closed first configuration to an open second configuration.

15. The surgical method of claim 14, wherein the contact of the first end surface with the second end surface second moves the blade portion from the open second configuration to an open third configuration, the blade portion being closer to the first longitudinal axis in the open second configuration than in the open third configuration.

16. A surgical method comprising:

creating an incision in the skin of a patient;

creating a surgical pathway from the incision to a surgical site within the patient;

attaching a first surface of a first member to the skin of the patient, the first member including the first surface, an opposite second surface, an aperture extending between the first surface and the second surface, and an arcuate groove provided on the second surface;

positioning a blade portion of a second expandable member in the pathway, and positioning a rim portion of second expandable member in a passageway of a third member between a flange portion of the third member and a fourth member rotatably disposed in the passageway;

rotatably translating the fourth member within the passageway to cause expansion of the second member by contacting a first end surface provided on the fourth member with a second end surface provided on the rim portion; and contacting one of a plurality of spaced apart teeth of a fifth member attached to the third member to the arcuate groove.

17. The surgical method of claim 16, wherein translation of the fourth member occurs along a first longitudinal axis of the passageway.

18. The surgical method of claim 17, wherein contact of the first end surface with the second end surface first moves the blade portion from a closed first configuration to an open second configuration.

19. The surgical method of claim 18, wherein the contact of the first end surface with the second end surface second moves the blade portion from the open second configuration to an open third configuration, the blade portion being closer to the first longitudinal axis in the open second configuration than in the open third configuration.

20. The surgical method of claim 16, wherein the arcuate groove comprises spaced apart first and second circular grooves each having a different radius of curvature; and further comprising removing the one of the plurality of spaced apart teeth from the first groove and inserting the one of the plurality of spaced apart teeth into the second groove to move the fifth member relative to the first member.

* * * * *

UNITED STATES PATENT AND TRADEMARK OFFICE
CERTIFICATE OF CORRECTION

Page 1 of 1

PATENT NO. : 10,080,561 B2
APPLICATION NO. : 15/848757
DATED : September 25, 2018
INVENTOR(S) : Lauchner It is certified that error appears in the above-identified patent and that said Letters Patent is hereby corrected as shown below:

In the Specification

In Column 4, Line 35, delete "GUM METAL®." and insert -- GUM METAL® --, therefor.

In Column 4, Line 50, delete "corticocancelous" and insert -- corticocancellous --, therefor.

In Column 4, Lines 58-59, delete "polyaetide, polyglycolide, polytymosine carbonate, polycaroplaetohe" and insert -- polypeptide, polyglycolide, polytyrosine carbonate, polycaprolactone --, therefor.

In Column 5, Line 13, delete "ring 22." and insert -- ring 24. --, therefor.

In Column 7, Line 7, delete "tooth 68" and insert -- tooth 68a --, therefor.

In Column 10, Line 54, delete "tooth 68" and insert -- tooth 68a --, therefor.

In the Claims

In Column 13, Line 28, in Claim 4, delete "positon" and insert -- position --, therefor.

In Column 14, Line 14, in Claim 11, delete "positon" and insert -- position --, therefor.

Signed and Sealed this
Fifth Day of February, 2019

Andrei Iancu
*Director of the United States Patent and Trademark Office*